United States Patent
Carrison

(10) Patent No.: US 7,112,205 B2
(45) Date of Patent: Sep. 26, 2006

(54) APPARATUS AND METHODS FOR DELIVERING COMPOUNDS INTO VERTEBRAE FOR VERTEBROPLASTY

(75) Inventor: Harold F. Carrison, Pleasanton, CA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 395 days.

(21) Appl. No.: 10/463,757

(22) Filed: Jun. 17, 2003

(65) Prior Publication Data

US 2004/0260303 A1 Dec. 23, 2004

(51) Int. Cl.
*A61B 17/58* (2006.01)
*A61F 2/00* (2006.01)

(52) U.S. Cl. .............................. 606/92; 606/93; 606/94

(58) Field of Classification Search .................. 606/93, 606/94, 95, 92, 213, 214, 215; 604/82, 28, 604/131, 187; 600/432
See application file for complete search history.

(56) References Cited

U.S. PATENT DOCUMENTS

| | | | |
|---|---|---|---|
| 1,612,996 A | 1/1927 | Herman | |
| 2,745,575 A | 5/1956 | Spencer | |
| 2,874,877 A | 2/1959 | Spencer | |
| 3,216,616 A | 11/1965 | Blankenship, Jr. | |
| 3,631,847 A * | 1/1972 | Hobbs, II | 600/432 |
| 4,274,163 A | 6/1981 | Malcom et al. | |
| 4,676,655 A | 6/1987 | Handler | |
| 4,944,065 A | 7/1990 | Svanberg et al. | |
| 4,966,601 A | 10/1990 | Draenert | |
| 4,983,164 A | 1/1991 | Hook et al. | |
| 5,193,907 A | 3/1993 | Faccioli et al. | |
| 5,219,897 A | 6/1993 | Murray | |
| 5,236,417 A * | 8/1993 | Wallis | 604/82 |
| 5,397,304 A | 3/1995 | Truckai | |
| 5,415,474 A | 5/1995 | Nelson et al. | |
| 5,431,654 A | 7/1995 | Nic | |
| 5,435,645 A | 7/1995 | Faccioli et al. | |
| 5,443,182 A | 8/1995 | Tanaka et al. | |
| 5,468,245 A | 11/1995 | Vargas, III | |
| 5,514,135 A | 5/1996 | Earle | |
| 5,545,460 A | 8/1996 | Tanaka et al. | |
| 5,549,381 A | 8/1996 | Hays et al. | |
| 5,681,317 A | 10/1997 | Caldarise | |
| 5,718,707 A | 2/1998 | Mikhail | |
| 5,824,087 A | 10/1998 | Aspden et al. | |

(Continued)

OTHER PUBLICATIONS

PCT International Search Report for PCT/US2004/015906, Applicant: Scimed Life Systems, Inc, Forms PCT/ISA/210 and 220, dated Oct. 10, 2004 (8 pages).

(Continued)

*Primary Examiner*—Pedro Philogene
(74) *Attorney, Agent, or Firm*—Vista IP Law Group, LLP

(57) ABSTRACT

An apparatus for delivering bone cement into a vertebra includes a cannula and a syringe pivotally coupled to the cannula. Preferably, the syringe is pivotally coupled to the cannula by a pivot fitting that may be detachable from one or both of the cannula and the syringe. The syringe includes a piston slidable in a barrel for advancing the bone cement through an outlet communicating with the cannula. A shaft and cable arrangement or a fluid-driven system may be used to advance the piston within the syringe. The cannula is inserted into a vertebra, and is connected to the syringe. The syringe is pivoted to a desired position, and bone cement is delivered from the syringe through the cannula and into the vertebra.

36 Claims, 3 Drawing Sheets

U.S. PATENT DOCUMENTS

| | | |
|---|---|---|
| 5,925,051 A | 7/1999 | Mikhail |
| 5,980,527 A | 11/1999 | Cohen et al. |
| 6,019,765 A | 2/2000 | Thornhill et al. |
| 6,045,555 A | 4/2000 | Smith et al. |
| 6,048,346 A | 4/2000 | Reiley et al. |
| 6,083,229 A | 7/2000 | Constantz et al. |
| 6,086,594 A | 7/2000 | Brown |
| 6,149,655 A | 11/2000 | Constantz et al. |
| 6,214,012 B1 | 4/2001 | Karpman et al. |
| 6,238,399 B1 | 5/2001 | Heller et al. |
| 6,241,734 B1 | 6/2001 | Scribner et al. |
| 6,273,916 B1 | 8/2001 | Murphy |
| 6,395,007 B1 | 5/2002 | Bhatnagar et al. |
| 6,406,175 B1 | 6/2002 | Marino |
| 6,439,439 B1 | 8/2002 | Rickard et al. |
| 6,478,808 B1 * | 11/2002 | Nowakowski ............. 606/213 |
| 6,502,608 B1 | 1/2003 | Burchett et al. |
| 6,676,664 B1 * | 1/2004 | Al-Assir ..................... 606/94 |
| 6,802,822 B1 * | 10/2004 | Dodge ......................... 604/82 |
| 6,917,828 B1 * | 7/2005 | Fukuda ...................... 600/432 |
| 6,953,461 B1 * | 10/2005 | McClurken et al. .......... 606/51 |
| 2002/0049448 A1 | 4/2002 | Sand et al. |
| 2004/0122438 A1 * | 6/2004 | Abrams ....................... 606/93 |

OTHER PUBLICATIONS

PCT Written Opinion of the International Search Authority for PCT/US2004/015906, Applicant: Scimed Life Systems, Inc, Form PCT/ISA/237, dated Oct. 10, 2004 (5 pages).

* cited by examiner

APPARATUS AND METHODS FOR DELIVERING COMPOUNDS INTO VERTEBRAE FOR VERTEBROPLASTY

FIELD OF THE INVENTION

The present invention relates generally to apparatus and methods for delivering compounds into a body, and more particularly to apparatus and methods for delivering bone cement, biomaterials, and/or other flowable compounds into vertebrae, e.g., during a vertebroplasty procedure.

BACKGROUND

Vertebroplasty is a procedure during which bone cement, biomaterials, and/or other flowable compounds are delivered into a vertebra. A syringe or other delivery device is generally provided within which the bone cement to be delivered is stored shortly before the bone cement is to be delivered. For example, the delivery device may include a barrel or housing including an open inlet end and an exit end with a narrow outlet. A plunger or threaded driver may be advanced into the inlet end to force bone cement within the barrel out the outlet in the exit end.

A cannula may be inserted percutaneously through the cutaneous layers of tissue above a hard tissue structure being treated and into the hard tissue structure. For example, the hard tissue structure may be a vertebra, and the cannula may include a sharpened tip to penetrate through cortical bone and into the cancellous bone within the vertebra. Alternatively, the hard tissue structure may be exposed using conventional surgical procedures before inserting the cannula and/or the cannula may be inserted over a needle previously placed or simultaneously advanced into the vertebra.

A semi-rigid or flexible tube, e.g., twenty to fifty centimeters long, may be connected between the proximal end of the cannula and the outlet of the delivery device to deliver bone cement via the tube into the hard tissue structure. The tube may be bent slightly during the procedure, e.g., to keep the user's hands and/or the delivery device out of the field of an imaging device, such as a fluoroscope, that may be used to monitor the procedure.

Alternatively, the syringe may be connected directly to the proximal end of the cannula. Such a rigid connection, however, requires a user to support the syringe/cannula combination, which may expose the user to x-ray radiation, e.g., from a fluoroscope used to monitor the injection of the material as it is being injected, requiring the user to wear appropriate additional x-ray protection, which may be cumbersome and inconvenient.

In addition, because of the high viscosity of bone cement, high pressures are generally required to inject bone cement from the delivery device, through the tube and cannula, and into the hard tissue structure. For example, pressures of up to one to three thousand pounds per square inch (1,000–3,000 psi) may be required to inject bone cement from the delivery device. This requires the user to apply substantial force, while simultaneously supporting the weight of the delivery device and its contents. This may cause fatigue of the user and/or undesired movement of the cannula delivery device during the procedure.

Accordingly, apparatus and methods for delivering bone cement or other compounds into vertebrae would be useful.

SUMMARY OF THE INVENTION

The present invention is directed to apparatus and methods for delivering compounds into a body, and more particularly to apparatus and methods for delivering bone cement, biomaterials, and/or other flowable compounds into vertebrae, e.g., during a vertebroplasty procedure.

In accordance with one aspect of the present invention, an apparatus is provided for delivering a compound into a tissue structure. Generally, the apparatus includes a cannula and a delivery device pivotally coupled to the cannula. The cannula may include a proximal end, a distal end having a size and shape for insertion into a tissue structure, and a lumen extending between the proximal end and an opening in the distal end.

The delivery device may include a barrel defining a cavity for receiving a flowable compound, e.g., bone cement, therein. The barrel may include a distal end including an outlet communicating with the cavity, the distal end being pivotally connected to the proximal end of the cannula such that the outlet communicates with the lumen of the cannula.

Preferably, the distal end of the barrel is pivotally coupled to the proximal end of the cannula by a pivot fitting. The pivot fitting may be detachable from one or both of the cannula and the delivery device, and/or the pivot fitting may be substantially permanently attached to one or both of the cannula and the delivery device.

In one embodiment, the delivery device may include a piston slidable within the barrel for delivering the compound therein through the outlet. Optionally, a nipple may extend from the piston into the cavity that may be received in the outlet when the piston is fully advanced.

Preferably, the barrel includes an opening in a proximal end thereof, and a shaft extends from the piston through the opening. The shaft and the opening may include mating thread patterns such that, as the shaft is rotated, the piston is advanced or retracted axially within the barrel.

Optionally, a cable may be provided, including a distal end coupled to the shaft, and a proximal end including an actuator. The actuator, e.g., a handle, may be rotated manually to cause the shaft to rotate to advance or retract the piston within the cavity. Alternatively, a motorized actuator may be coupled to the proximal end of the cable to rotate the cable and deliver the compound in the delivery device at a desired pressure and/or flow rate.

In another alternative, a tube may be connected to the opening of the barrel instead of the shaft and/or cable. A fluid may be delivered or evacuated from the barrel to cause the piston to move within the barrel.

In accordance with another aspect of the present invention, a method is provided for delivering a flowable compound, e.g., bone cement, into a hard tissue structure of a patient, such as a vertebra. A distal end of a cannula may be inserted into the tissue structure to be treated, e.g., percutaneously or after surgically exposing the tissue structure. A proximal end of the cannula may be connected to a delivery device using a pivot fitting. The delivery device may be pivoted and/or otherwise manipulated relative to the cannula to a desired position. The compound may be delivered from the delivery device through the cannula and into the tissue structure, and then the cannula may be removed from the tissue structure.

Other objects and features of the present invention will become apparent from consideration of the following description taken in conjunction with the accompanying drawings.

DETAILED DESCRIPTION OF THE PREFERRED EMBODIMENTS

Figure 1:
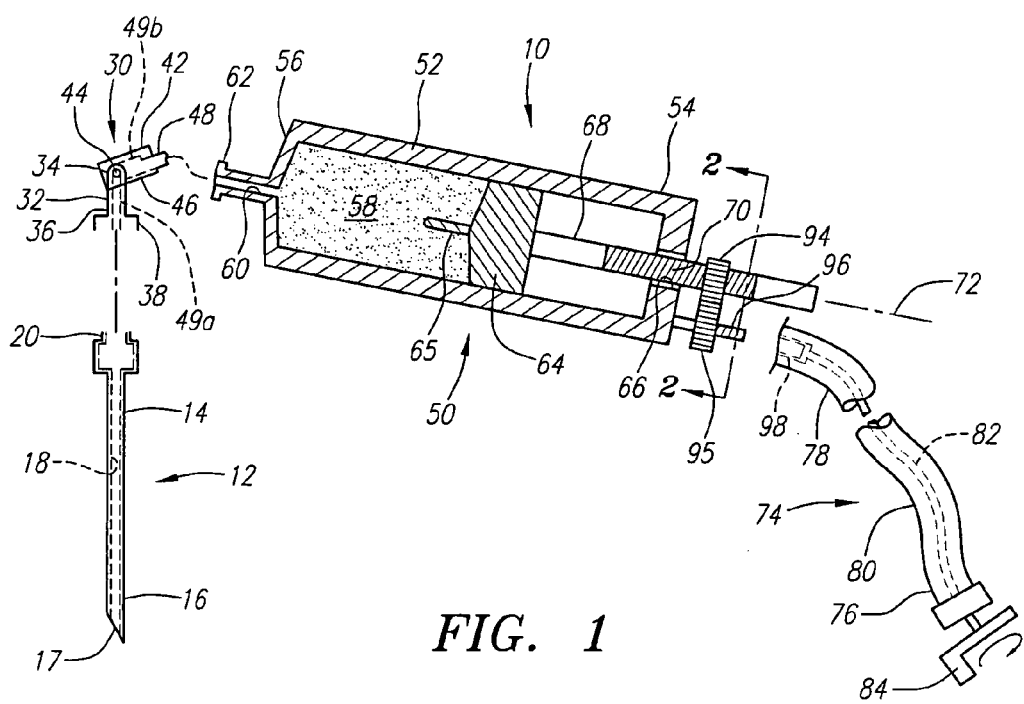
FIG. 1 is a partial cross-sectional side view of a first preferred embodiment of an apparatus for delivering bone cement into a vertebra, in accordance with the present invention.

Turning to the drawings, FIG. 1 shows a first preferred embodiment of an apparatus 10 for delivering bone cement, biomaterial, and/or other compounds into a vertebra or other hard tissue structure (not shown). Generally, the apparatus 10 includes a cannula 12, a syringe or other delivery device 50, a pivot fitting 30 for pivotally connecting the cannula 12 to the syringe 50, and a cable 74.

Generally, the cannula 12 is a substantially rigid elongate tubular member including a proximal end 14, a distal end 16, and a lumen 18 extending therebetween. The cannula 12 may be a needle, i.e., including a beveled or otherwise sharpened distal tip 17 such that the distal end 16 may penetrate into hard tissue, such as bone, although alternatively the cannula 12 may have a substantially blunt distal tip (not shown). A luer lock or other connector 20 may be provided on the proximal end 14 for attaching the cannula to the pivot fitting 30, as explained further below.

The cannula 12 may have a substantially uniform diameter or cross-section, similar to known needles for accessing a vertebra, e.g., between about eleven and thirteen gauge (11–13 GA). Alternatively, the cannula 12 may taper from the proximal end 14 at least partially towards the distal end 16, e.g., such that the distal end 16 corresponds to a conventional needle diameter. The cannula 12 may be formed from conventional materials, e.g., stainless steel, metals, plastics, laminated tubes, and the like.

The pivot fitting 30 generally includes first and second portions, e.g., a tubular segment 32 and a hollow housing 42 that are pivotally coupled to one another. The tubular segment 32 may include a first end 34 coupled to the housing 42 and a second end 36 terminating in a connector 38, e.g., a male or female luer lock connector. The housing 42 may include a socket (not shown) for receiving the first end 34 of the tubular segment 32 such that the tubular segment 32 is free to pivot relative to the housing 42. A second end 46 of the housing 42 includes a connector 48 thereon, such as a male or female luer lock connector.

In one embodiment, the pivot fitting 30 may have a single degree of freedom. For example, the tubular segment 32 may include opposing tabs 44 (only one shown in FIG. 1), defining a transverse axis, and the housing 42 may include sockets (not shown) for receiving the tabs such that the tubular segment 32 may pivot about the transverse axis relative to the housing 42. Alternatively, the pivot fitting 30 may include multiple degrees of freedom. For example, the tubular segment 32 may be connected to the housing 42 by a ball and socket joint (not shown), thereby allowing the tubular segment 32 to pivot about a central axis (also not shown).

The tubular segment 32 and the housing 42 define a lumen 49 therein that extends between the second ends 36, 46. For example, the lumen 49 may include a segment 49a that extends between the first and second ends 34, 36 of the tubular segment 32, and a segment 49b that extends from the socket to the second end 46 of the housing 42. Preferably, the lumen 49 remains substantially open throughout the pivotal movement of the tubular segment 32 relative to the housing 42. Thus, the lumen 49 may provide a substantially fluid-tight passage that extends between the second ends 36, 46 of the tubular segment 32 and housing 42 to allow bone cement or other flowable compounds to pass through the pivot fitting 30 without substantial leakage.

The tubular segment 32 and the housing 42 are formed from a variety of materials capable of handling the internal pressures experienced when bone cement is delivered, e.g., between about one and three thousand pounds per square inch (1,000–3,000 psi). In addition, the pivot fitting 30 should be sufficiently strong to support any bending or other forces experienced when the pivot fitting 30 is used to couple a cannula 12 to a syringe 50 during a vertebroplasty procedure.

In alternative embodiments, the pivot fitting 30 may be substantially permanently attached to at least one of the cannula 12 and the syringe 50. For example, in one embodiment, the pivot fitting 30 may be provided as part of the syringe 50, i.e., extending from a distal end 56 of the syringe 50, thereby eliminating connectors 48, 58 between the pivot fitting 30 and the syringe 50 (not shown). The other end of the pivot fitting 30 may have a connector 38, e.g., a luer lock, as explained above. Alternatively, the pivot fitting 30 may be substantially permanently attached to the proximal end 14 of the cannula 12 (also not shown). Thus, one or both ends of the pivot fitting 30 may be detachable from and/or substantially permanently attached to the cannula 12 and/or syringe 50.

With continued reference to FIG. 1, the syringe 50 generally includes a barrel 52 including a proximal end 54, and a distal end 56, thereby defining an interior space or cavity 58 within which a flowable compound, such as bone cement and/or biomaterials (not shown), may be contained. The distal end 56 may include an outlet port 60 communicating with the cavity 58. A luer lock or other connector 62 may be provided on the outlet port 60 for cooperating with a complementary connector, such as one of the connectors 38, 48 on the pivot fitting 30.

A piston 64 may be inserted into the proximal end 54 of the barrel 52 or otherwise slidably disposed within the cavity 58 for forcing a compound within the barrel 52 out through the outlet port 60. The piston 64 may be advanced distally, thereby applying a force creating sufficient pressure to inject the compound within the barrel 52 out the outlet port 60. Optionally, the piston 64 may include a nipple 65 extending into the cavity 58. The nipple 65 may have a size corresponding to the outlet port 60 of the syringe 50, e.g., such that the nipple 65 may be slidably received in the outlet port 60 as the piston 64 is depressed distally. This may minimize the amount of bone cement remaining within the syringe 50 when the piston 64 is fully depressed.

Preferably, the proximal end 54 of the barrel 52 is substantially closed and/or includes a threaded opening 66 therethrough. A plunger, screw, or other substantially rigid shaft 68 may extend from the piston 64 through the threaded opening 66. The shaft 68 may include a threaded region 70 that may mate with the thread pattern in the threaded opening 66 such that rotation of the shaft 68 about its longitudinal axis 72 causes the shaft 68, and consequently, the piston 64 to move axially, i.e., to advance and/or retract the piston 64 within the barrel 52.

A screw mechanism may be coupled to the shaft 68 for causing the shaft 68 to rotate relative to the barrel 52, e.g., to facilitate advancing and/or retracting the piston 64. For example, a cable 74 may be provided that includes a proximal end 76 and a distal end 78 that is coupled to the shaft 68. Alternatively, the threaded opening 66 may be eliminated, and the shaft 68 may terminate in a thumb or ring (not shown) that may be used to push directly on the shaft 68, and consequently, advance the piston 64 axially to deliver bone cement from the cavity 68.

In a preferred embodiment, the cable 74 is a substantially flexible elongate member, e.g., having sufficient length such that the proximal end 76 of the cable 74 may be disposed away from a patient, and preferably from a field of an imaging device, e.g., fluoroscope, as explained further below. For example, the cable 74 may have a length between about twenty and fifty centimeters (20–50 cm).

The cable 74 may include an outer sleeve 80 and an elongate inner member 82 extending through the outer sleeve 80 and rotatable within the outer sleeve 80. Preferably, the inner member is formed from one or more wires, e.g., a braid of wires or rod of stainless steel or other material, that are flexible yet have sufficient torsional rigidity that rotation at the proximal end 76 of the cable 74 may be effectively transferred to the distal end 78, i.e., to rotate the shaft 68. The outer sleeve 80 may be provided from a variety of materials, e.g., plastic, metal, and/or fabric that may surround the inner member 82. Preferably, the outer sleeve 80 has a substantially lubricious inner surface, e.g., to allow the inner member 82 to rotate freely within the outer sleeve 80.

A handle or other actuator 84 may be provided on the proximal end 76 of the cable 74, e.g., coupled to the inner member 82 to facilitate rotating the inner member 92 relative to the outer sleeve 80. For example, the actuator 84 may be a simple handle, as shown in FIG. 1, that may be rotated manually to rotate the cable 74. Alternatively, the actuator 84 may include a motor (not shown) that may be used to rotate the cable 74 using electrical, pneumatic, or other power sources. One possible advantage of a motorized actuator is that the pressure applied to the bone cement may be controlled more precisely. In addition, a motorized actuator may be controlled remotely, e.g., from outside the room where the patient is being treated, thereby reducing exposure of medical personnel to x-rays and the like.

Figure 2:
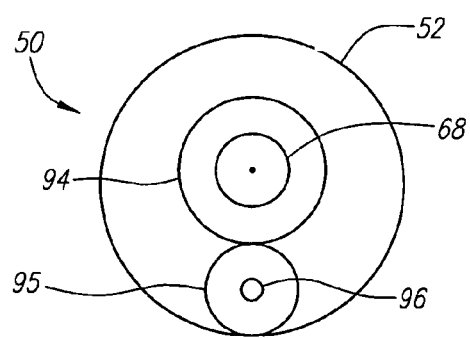
FIG. 2 is a cross-sectional view of the apparatus of FIG. 1, taken along line 2—2.

The distal end 78 of the cable 74 and the shaft 68 may including cooperating elements for translating rotation of the cable 74, specifically the inner member 82, to rotation of the shaft 68. For example, as best seen in FIGS. 1 and 2, the distal end 78 of the cable 74 and the shaft 68 may include mating gears 94, 95 having teeth or other elements that cooperate such that the shaft 68 rotates when the cable 74, and, specifically, the inner member 82, is rotated.

Optionally, the cable 74 may be detachable from the gear 94 and/or syringe 50. For example, the gear 94 may include a threaded hub 96, and the inner member 82 of the cable 74 may terminate in a threaded sleeve 98 within which the hub 96 may be threaded or otherwise secured. Alternatively, the cable 74 may be substantially permanently connected to the gear 95. In another option, the outer sleeve 80 may be fixed, e.g., by a clip and the like (not shown) to the barrel 52, to prevent the outer sleeve 80 from twisting as the inner member 82 is rotated. Thus, from a location away from the syringe 50, e.g., outside a field of a fluoroscope used to monitor the procedure, the cable 74 may be used to advance the piston 64 to deliver bone cement or other compound from the cavity 58 of the syringe 52, as explained further below.

Figure 3:
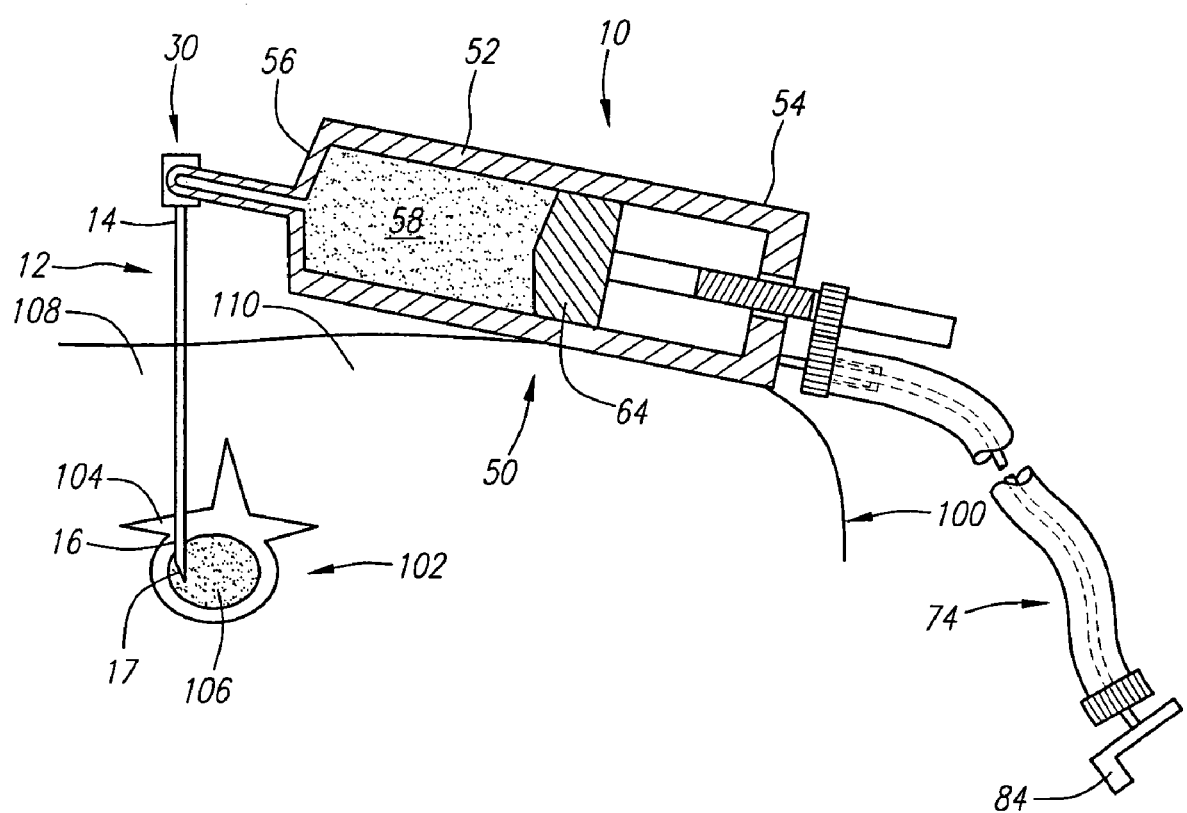
FIG. 3 is a partial cross-sectional view of a patient's body, showing a method for delivering bone cement into a vertebra using the apparatus of FIG. 1.

Turning to FIG. 3, the apparatus 10 may be used to deliver bone cement, biomaterials, and/or other flowable compounds into a hard tissue structure, such as a vertebra 102, within a patient's body 100. It will be appreciated that the apparatus 10 may be used to treat other bones or hard tissue structures as well (not shown), in addition to vertebra 102. The compound may include any known material, such as those disclosed in published PCT applications WO 02/064062 and WO 99/49819, the disclosures of which are expressly incorporated herein by reference.

If the distal end 16 of the cannula 12 includes a sharpened distal tip 17, the distal tip 17 may be inserted directly into the vertebra 102, e.g., until the distal end 16 penetrates the cortical bone 104 and enters the cancellous bone region 106 therein. The cannula 12 may be inserted percutaneously, e.g., through cutaneous fat, muscle, and/or other tissue 108 overlying the vertebra 102. Alternatively, the vertebra 102 may be at least partially exposed before inserting the cannula 12, e.g., using an open surgical procedure (not shown). For example, the tissue 108 overlying the vertebra 102 may be surgically dissected and/or retracted (not shown) to expose the vertebra 102, and the distal end 16 of the cannula 12 may be inserted into the exposed vertebra 102.

In one embodiment (if the cannula 12 is initially separate from the pivot fitting 30 and/or the syringe 50), an obturator or other device (not shown) may be inserted into the lumen 18 of the cannula 12 to prevent tissue and/or fluid, such as blood, from entering the lumen 18 while the cannula 12 is advanced through tissue. In a further alternative, a stylet and sheath (not shown) may be percutaneously inserted through the overlying tissue 108 to access the vertebra 102. The stylet may be removed from within the sheath, and the cannula 12 may be advanced through the sheath and then inserted into the vertebra 102.

It will be appreciated that any known open or minimally invasive procedure may be used to place the cannula 12 into the vertebra 102. In addition, it will be appreciated that the insertion of the cannula 12 may be monitored using external imaging, such as fluoroscopy, ultrasound imaging, magnetic resonance imaging ("MRI"), and the like (not shown). For example, the cannula 12 may be formed from radiopaque material and/or may include one or more radiopaque markers to facilitate monitoring the position of the cannula 12 as it is advanced into the vertebra 102 using a fluoroscope, as is known in the art.

Once the distal end 16 of the cannula 12 is inserted into the vertebra 102, the syringe 50 (with bone cement or other compound provided therein using conventional methods) may be connected to the proximal end 14 of the cannula 12. For example, the pivot fitting 30 may be connected first (or, alternatively, may be substantially permanently attached) to the distal end 56 of the syringe 50. The loose end (e.g., end 36 of the tubular segment 32 shown in FIG. 1) may be connected to the proximal end 14 of the cannula 12, e.g., by connecting mating luer lock connectors 20, 38.

Alternatively, the pivot fitting 30 may be substantially permanently attached to the proximal end 14 of the cannula 12, and then may be attached to the distal end 56 of the syringe 50, e.g., using mating luer lock connectors 48, 62 (not shown, see FIG. 1). In a further alternative, the pivot fitting 30 may be substantially permanently attached to both the cannula 12 and the syringe 50 (not shown), such that the syringe 50 is attached to the cannula 12 when the cannula 12 is inserted into the vertebra 102.

Once the apparatus 10 is assembled, the syringe 50 may be disposed at a desired angle relative to the cannula 12. For example, it may be desirable to lie the syringe 50 on the patient's skin 110 (e.g., on the patient's back) overlying the vertebra 102. This will avoid a physician or other individual from having to support the syringe 50 while bone cement or other compound is delivered from the syringe 50 into the vertebra 102. In addition, resting the syringe on the patient's body 100 may remove the weight of the syringe 50 and its contents from the cannula 12, thereby minimizing the risk of bending or otherwise damaging the cannula 12.

Because the syringe 50 may be located within the field of an imaging system, e.g., a fluoroscope (not shown), it may be desirable to extend the cable 74 away from the patient's body 100, e.g., until the actuator 84 is located outside the field of the imaging system. This will remove the operator of the cable 74 away from the field, thereby substantially reducing their exposure to radiation and the like.

Once the syringe 50 and/or cable 74 are disposed at a desired location, the piston 64 may be advanced to deliver the bone cement or other compound from the syringe 50 through the pivot fitting 30 and the cannula 12 into the cancellous bone region 106 of the vertebra 102. Because the path through which the bone cement passes is substantially shorter than the path when conventional tubing is used to connect a syringe to a cannula (not shown), less pressure may be required to deliver the bone cement than using such tubing systems. In addition, less bone cement may be wasted, because the flow path may have less volume that must be filled with bone cement before the bone cement exits the cannula 12 and enter the vertebra 102.

Optionally, a motorized actuator (not shown) may be coupled to the cable 74, rather than the manual actuator handle 84 shown. This may allow more precise regulation of the pressure and/or flow rate used to deliver the bone cement into the vertebra 102. In addition, a motorized actuator may be operated from outside the room, e.g., from an observation area, thereby reducing exposure of medical personnel to radiation from a fluoroscope or other devices.

Once sufficient bone cement is delivered into the vertebra 102, the cannula 12 may be removed and the puncture or other access opening may be closed using conventional procedures.

Figure 4:
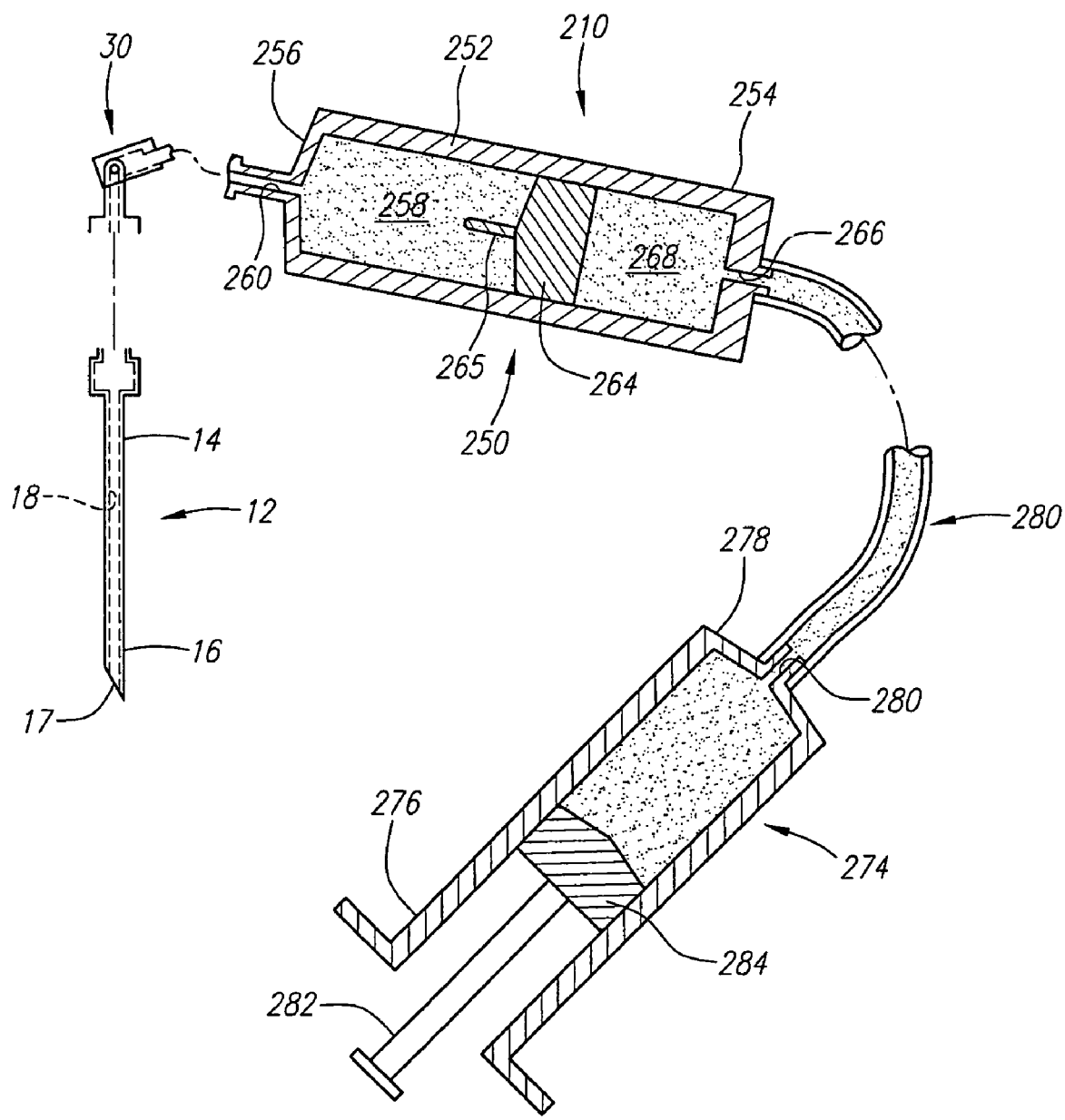
FIG. 4 is a partial cross-sectional side view of a second preferred embodiment of an apparatus for delivering bone cement into a vertebra, in accordance with the present invention.

Turning to FIG. 4, another preferred embodiment of an apparatus 210 is shown for delivering bone cement, biomaterial, and/or other compounds into a vertebra or other hard tissue structure (not shown). Generally, the apparatus 210 includes a cannula 212, a syringe or other delivery device 250, and a pivot fitting 230 for pivotally connecting the cannula 212 to the syringe 250, similar to the previous embodiment.

The syringe 250 generally includes a barrel 252 including a proximal end 254 and a distal end 256, thereby defining an interior space or cavity 258 within which a flowable compound, such as bone cement and/or biomaterials, may be contained. The distal end 256 may include an outlet port 260 communicating with the cavity 258.

A piston 264 may be inserted into the proximal end 254 of the barrel 252 or otherwise slidably disposed within the cavity 258 for forcing a compound within the barrel 252 out through the outlet port 260. Optionally, similar to the previous embodiment, the piston 264 may include a nipple 265 extending into the cavity 258. Preferably, the proximal end 254 of the barrel 252 is substantially closed, thereby defining a proximal chamber 268, and includes an opening 266 communicating with the proximal chamber 268.

Unlike the previous embodiment, another syringe 274 may be connected to the barrel 252 for delivering a fluid into the proximal chamber 268. For example, the syringe 274 may include a barrel 276 including proximal and distal ends 276, 278, an outlet 280 in the distal end 278, and a plunger 282 and/or piston 284 slidably inserted into the proximal end 276 thereof. Tubing 288 may extend between the outlet 278 and the opening 266 for delivering a fluid, e.g., saline, between a cavity 288 of the syringe 274 and the proximal chamber 268 of the syringe 250. The tubing 286, opening 266, and/or outlet 278 may include cooperating connectors, e.g., luer lock connectors, (not shown) or the syringe 250 may include a nipple over which the tubing 288 may be secured simply by an interference fit for removably attaching the tubing 286 to the syringes 250, 274. Alternatively, the tubing 286 may be substantially permanently attached to one or both of the syringes 250, 274.

The apparatus 210 may be used to deliver bone cement or other flowable materials into a vertebra or other bone structure (not shown), similar to the previous embodiment. To advance the piston 264 and inject bone cement into the cannula 12, the plunger 282 and piston 284 may be advanced distally to deliver the saline or other fluid through the tubing 280 into the proximal chamber 268. This forces the piston 264 distally, thereby forcing the bone cement out of the cavity 258 and into and/or through the pivot fitting 30 and cannula 12. Alternatively, a pump or other device (not shown) may be provided instead of the syringe 274 to automatically and/or controllably advance the piston 264 within the barrel 252.

This embodiment may allow bone cement to be delivered without subjecting the syringe 250 to torque. In contrast, the threaded shaft/cable arrangement described above (and shown in FIG. 1) may subject the syringe 50 and/or other components of the apparatus 10 to torque due to rotation of the inner member 82 of the cable 74.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. An apparatus for delivering bone cement into a vertebra, comprising:
   a cannula comprising a proximal end, a distal end having a size and shape for insertion into a vertebra, and a lumen extending between the proximal end and an opening in the distal end; and
   a delivery device comprising a barrel and a piston, the barrel defining a cavity for receiving a flowable compound therein, the barrel having a distal end comprising an outlet communicating with the cavity, the distal end of the barrel being pivotally connected to the proximal end of the cannula via only one pivot joint such that the outlet communicates with the lumen of the cannula, the piston being slidable within the cavity of the barrel for delivering the flowable compound therein through the outlet.

2. The apparatus of claim 1, further comprising a flowable compound in the cavity.

3. The apparatus of claim 2, wherein the flowable compound comprises bone cement.

4. The apparatus of claim 1, wherein the barrel comprises a threaded opening, and wherein a shaft coupled to the piston extends through the threaded opening, the shaft comprising a thread pattern thereon for mating with the threaded opening such that rotation of the shaft advances or retracts the piston axially within the cavity.

5. The apparatus of claim 1, wherein the distal end of the barrel is pivotally coupled to the proximal end of the cannula by a pivot fitting.

6. The apparatus of claim 5, wherein the pivot fitting is detachable from the proximal end of the cannula.

7. The apparatus of claim 5, wherein the pivot fitting is detachable from the distal end of the barrel.

8. The apparatus of claim 1, wherein the pivot fitting comprises a tubular member pivotable relative to a hollow housing, wherein one of the tubular member and the housing is connected to the distal end of the barrel and the other of the tubular member and the housing is connected to the proximal end of the cannula, thereby providing a flow path between the outlet and the lumen.

9. An apparatus for delivering bone cement into a vertebra, comprising:
a cannula comprising a proximal end, a distal end having a size and shape for insertion into a vertebra, and a lumen extending between the proximal end and an opening in the distal end;
a delivery device comprising a barrel defining a cavity for receiving a flowable compound therein, a distal end comprising an outlet communicating with the cavity, a piston slidable within the cavity of the barrel for delivering the flowable compound therein through the outlet, and a shaft coupled to the piston and having a thread pattern thereon for mating with the threaded opening such that rotation of the shaft advances the piston axially within the cavity, the distal end being pivotally connected to the proximal end of the cannula such that the outlet communicates with the lumen of the cannula;
a cable coupled to the shaft; and
an actuator coupled to the cable, wherein rotation of the actuator causes rotation of the shaft to advance the piston within the cavity.

10. The apparatus of claim 9, wherein the cable comprises an outer sleeve and an inner member extending through the outer sleeve from the actuator to the shaft.

11. The apparatus of claim 9, wherein the shaft and the distal end of the cable comprise cooperating gears for translating rotation of the cable to rotation of the shaft.

12. An apparatus for delivering bone cement into a vertebra, comprising:
a cannula comprising a proximal end, a distal end having a size and shape for insertion into a vertebra, and a lumen extending between the proximal end and an opening in the distal end;
a delivery device comprising a barrel defining a cavity for receiving a flowable compound therein, a distal end comprising an outlet communicating with the cavity, and a piston slidable within the cavity of the barrel for delivering the flowable compound therein through the outlet, wherein the piston divides the cavity into a distal region for receiving a flowable compound therein and a proximal region, the distal end being pivotally connected to the proximal end of the cannula such that the outlet communicates with the lumen of the cannula;
a source of fluid communicating with the proximal region of the cavity via tubing for delivering fluid into the proximal region to advance the piston distally within the barrel.

13. The apparatus of claim 12, wherein the source of fluid comprises a syringe or pump.

14. The apparatus of claim 12, further comprising flexible tubing connecting the source of fluid to the delivery device such that fluid from the source of fluid may flow through the tubing into the proximal region.

15. The apparatus of claim 14, wherein the tubing is removably connected to at least one of the source of fluid and the delivery device.

16. The apparatus of claim 14, wherein the tubing is permanently connected to at least one of the source of fluid and the delivery device.

17. A method for delivering bone cement into a vertebra of a patient, the method comprising:
inserting a distal end of a cannula into the vertebra;
connecting a proximal end of the cannula to a delivery device comprising bone cement therein using a pivot fitting, the delivery device comprising a cable coupled to a piston within the delivery device;
pivoting the delivery device relative to the cannula to a desired position;
rotating the cable, thereby causing the piston to advance within the delivery device to deliver the bone cement from the delivery device through the cannula and into the vertebra; and
removing the cannula from the vertebra.

18. The method of claim 17, further comprising imaging the vertebra with an imaging device, and wherein the cable comprises an actuator disposed outside a field of the imaging device, the actuator being activated to rotate the cable.

19. A method for delivering a flowable compound into a hard tissue structure of a patient, the method comprising:
inserting a distal end of a cannula into the tissue structure to be treated;
pivotally connecting a proximal end of the cannula to a barrel via only one pivot joint, the barrel containing a flowable compound therein;
pivoting the barrel relative to the cannula to a desired position;
delivering the compound from the barrel through the cannula and into the tissue structure; and
removing the cannula from the tissue structure.

20. The method of claim 19, wherein the cannula is inserted percutaneously through cutaneous tissue overlying the tissue structure before being inserted into the tissue structure.

21. The method of claim 19, wherein the cannula is inserted into the tissue structure before the proximal end of the cannula is connected to the delivery device.

22. The method of claim 19, wherein the compound comprises at least one of bone cement and biomaterial.

23. The method of claim 19, wherein the hard tissue structure comprises a vertebra.

24. The method of claim 19, wherein the cannula comprises a sharpened distal tip that penetrates through cortical bone of the vertebra into cancellous bone of the vertebra as the cannula is inserted into the vertebra.

25. The method of claim 19, wherein the delivery device is pivoted until the delivery device rests on the patient's skin.

26. The method of claim 19, further comprising distally displacing a piston within the barrel to deliver the compound.

27. A method for delivering a flowable compound into a hard tissue structure of a patient, the method comprising:
inserting a distal end of a cannula into the tissue structure to be treated;
pivotally connecting a proximal end of the cannula to a delivery device comprising a flowable compound therein;
pivoting the delivery device relative to the cannula to a desired position;

delivering the compound from the delivery device through the cannula and into the tissue structure by rotating a cable coupled to a piston slidably disposed within the delivery device to advance the piston within the delivery device; and removing the cannula from the tissue structure.

28. The method of claim 27, further comprising imaging the tissue structure being treated with an imaging device, and wherein the cable comprises an actuator disposed outside a field of the imaging device.

29. The method of claim 28, wherein the delivery device is at least partially exposed within the field of the imaging device.

30. The method of claim 27, wherein the cable is coupled to a shaft extending from the piston, and wherein the cable is rotated to rotate the shaft, thereby advancing the piston within the barrel.

31. The method of claim 30, wherein the cable and the shaft are rotatably coupled to one another by cooperating gears.

32. The method of claim 27, wherein another end of the cable is coupled to a motor, and wherein the motor is activated to rotate the cable and advance the piston within the barrel.

33. A method for delivering a flowable compound into a hard tissue structure of a patient, the method comprising:

inserting a distal end of a cannula into the tissue structure to be treated;

pivotally connecting a proximal end of the cannula to a delivery device comprising a flowable compound therein, wherein a piston is slidable within the delivery device, thereby defining a proximal chamber within the delivery device;

pivoting the delivery device relative to the cannula to a desired position;

delivering the compound from the delivery device through the cannula and into the tissue structure by delivering a fluid into the proximal chamber to advance the piston within the delivery device; and removing the cannula from the tissue structure.

34. The method of claim 33, further comprising imaging the tissue structure being treated with an imaging device, and wherein the tubular member is coupled to at least one of a syringe and pump disposed outside a field of the imaging device for delivering the fluid into the proximal chamber.

35. The method of claim 33, further comprising connecting a source of fluid to the delivery device, the fluid being delivered into the proximal chamber from the source of fluid.

36. The method of claim 35, wherein the source of fluid is connected to the delivery device by flexible tubing.

* * * * *